(12) United States Patent
Kutschbach et al.

(10) Patent No.: US 6,840,622 B2
(45) Date of Patent: Jan. 11, 2005

(54) METHOD AND SYSTEM FOR DETERMINING THE TOPOGRAPHY FOR REACTION SIGNALS OF AN EYE

(75) Inventors: Ernst Kutschbach, deceased, late of Chemnitz (DE); by Johanna Jutta Kutschbach, legal representative, Chemnitz (DE); Jens Grünewald, Limbach-Oberfrohna (DE)

(73) Assignee: Medizin & Service GmbH, Niederweisa (DE)

( * ) Notice: Subject to any disclaimer, the term of this patent is extended or adjusted under 35 U.S.C. 154(b) by 340 days.

(21) Appl. No.: 10/168,147

(22) PCT Filed: Dec. 11, 2000

(86) PCT No.: PCT/DE00/04395
§ 371 (c)(1),
(2), (4) Date: Jul. 16, 2002

(87) PCT Pub. No.: WO01/43637
PCT Pub. Date: Jun. 21, 2001

(65) Prior Publication Data
US 2004/0189940 A1 Sep. 30, 2004

(30) Foreign Application Priority Data
Dec. 13, 1999 (DE) .......................... 199 59 881

(51) Int. Cl.[7] .............................................. A61B 3/00
(52) U.S. Cl. ...................................... 351/200; 600/558
(58) Field of Search ........................ 351/200, 205, 351/206, 211, 213, 221, 246; 600/558

(56) References Cited

U.S. PATENT DOCUMENTS 4,304,242 A * 12/1981 Siarkiewicz et al. ........ 600/558
6,022,107 A * 2/2000 Kutschbach et al. ........ 351/200

FOREIGN PATENT DOCUMENTS

DE  19649858 A  * 6/1998  ......... A61B/5/0484
JP  03297443 A  * 12/1991  ......... A61B/5/0476

OTHER PUBLICATIONS

Parks, S. et al.: "Comparison of repeattability of the multi-focal electroretinogram and Humphrey perimeter", Documenta Ophthalmologica, vol. 92, 1997, pp. 281–289.*
Jiang, X. et al.: "Measurement of teh micro–electroretinogram and component analysis", Medical and Biological Engineering and Computing, vol. 31, Jul. 1993, pp. 73–79.*
Fadda, A. et al: "Instrumentation for electroretinography: a LED–based stimulator", Annual International Conference of teh IEEE Engineering in Medicine and Biology Society, Oct. 31, 1996, pp. 152–153.*

* cited by examiner

Primary Examiner—Brian L. Casler
Assistant Examiner—John R. Sanders
(74) Attorney, Agent, or Firm—Laurence A. Greenberg; Werner H. Stemer; Ralph E. Locher

(57) ABSTRACT

The invention relates to a method and system for determining the topography for reaction signals of an eye. The reaction signals of cyclic luminous excitations are simultaneously measured on partial surfaces of the retina by using, for each partial surface, another integer number of oscillations in a predetermined time segment. These oscillations are derived from a clock rate. In the time segment, a smaller number of oscillations occur by prolonging a clock pulse by an appointed interval, and a greater number of oscillations occur by shortening the clock pulse by an appointed interval. The cumulative signal recorded on the patient contains the sum of the reaction signals and is digitized in an amplified and filtered manner with the clock pulse for generating the oscillations. The reaction signals of the individual partial surfaces are recovered by cyclic summation. This is effected by, for the corresponding partial surfaces, removing values at the prolonged locations or inserting the mean values of adjacent measuring points at the shortened locations.

10 Claims, 6 Drawing Sheets

| Total Number of Oscillations | Number of oscillations with | | | | | Spacing of the change in clock pulse |
|---|---|---|---|---|---|---|
| | 65 Clock pulses | 66 Clock pulses | 67 Clock pulses | 68 Clock pulses | 69 Clock pulses | |
| 1080 | 930 | 150 | | | | 35 |
| 1079 | 864 | 215 | | | | |
| 1078 | 798 | 280 | | | | |
| 1077 | 732 | 345 | | | | |
| 1076 | 666 | 410 | | | | |
| 1075 | 600 | 475 | | | | 42 |
| 1074 | 534 | 540 | | | | |
| 1073 | 468 | 605 | | | | |
| 1072 | 402 | 670 | | | | |
| 1071 | 336 | 735 | | | | 50 |
| 1070 | 270 | 800 | | | | |
| 1069 | 204 | 865 | | | | |
| 1068 | 138 | 930 | | | | |
| 1067 | 72 | 995 | | | | |
| 1066 | 6 | 1060 | | | | |
| 1065 | | 1005 | 60 | | | 70 |
| 1064 | | 938 | 126 | | | 75 |
| 1063 | | 871 | 192 | | | |
| 1062 | | 804 | 258 | | | |
| 1061 | | 637 | 324 | | | |
| 1060 | | 570 | 390 | | | 105 |
| 1059 | | 603 | 466 | | | |
| 1058 | | 536 | 522 | | | |
| 1057 | | 469 | 588 | | | 150 |
| 1056 | | 402 | 654 | | | 175 |
| 1055 | | 335 | 720 | | | 210 |
| 1054 | | 268 | 786 | | | |
| 1053 | | 201 | 852 | | | 350 |
| 1052 | | 134 | 918 | | | 525 |
| 1051 | | 67 | 984 | | | 1050 |
| 1050 | | | 1050 | | | – |
| 1049 | | | 982 | 67 | | 1050 |
| 1048 | | | 914 | 134 | | 525 |
| 1047 | | | 846 | 201 | | 350 |
| 1046 | | | 778 | 268 | | |
| 1045 | | | 710 | 335 | | 210 |
| 1044 | | | 642 | 402 | | 175 |
| 1043 | | | 574 | 469 | | 150 |
| 1042 | | | 506 | 536 | | |
| 1041 | | | 438 | 603 | | |
| 1040 | | | 370 | 570 | | 105 |
| 1039 | | | 302 | 637 | | |
| 1038 | | | 234 | 804 | | |
| 1037 | | | 166 | 871 | | |
| 1036 | | | 98 | 938 | | |
| 1035 | | | 30 | 1005 | | |
| 1034 | | | | 996 | 38 | 75 |
| 1033 | | | | 927 | 106 | 70 |
| 1032 | | | | 858 | 174 | |
| 1031 | | | | 789 | 242 | |
| 1030 | | | | 720 | 310 | |
| 1029 | | | | 651 | 378 | 50 |
| 1028 | | | | 582 | 446 | |
| 1027 | | | | 513 | 514 | |
| 1026 | | | | 444 | 582 | |
| 1025 | | | | 375 | 650 | 42 |
| 1024 | | | | 306 | 718 | |
| 1023 | | | | 237 | 786 | |
| 1022 | | | | 168 | 854 | |
| 1021 | | | | 99 | 922 | |
| 1020 | | | | 30 | 990 | 35 |
| N | | | | | | 1050:ΔN |

Fig. 5

METHOD AND SYSTEM FOR DETERMINING THE TOPOGRAPHY FOR REACTION SIGNALS OF AN EYE

CROSS-REFERENCE TO RELATED APPLICATIONS

This application claims priority from German Application No. 19959881.9, filed Dec. 13, 1999, and is a national-stage entry of International Application No. PCT/DE00/04395, filed Dec. 11, 2000.

BACKGROUND OF THE INVENTION

Field of the Invention

The invention relates to a method and a system for determining the topography for reaction signals of an eye, partial surfaces of the retina being cyclically stimulated and, in the process, the total reaction of the eye in the steady state being measured.

The determined topography for the reaction signals of an eye shows the objective sensitivity distribution of the retina and therefore provides information on the visual faculty. Eye diseases, for example glaucoma, can be detected early and assessed with the aid of such an examination. Above all, partial defects of the retina can be established with the aid of such examinations.

There are a multiplicity of examination methods that operate on a subjective basis, that is to say in which the patient examined evaluates the measurement by his statement. In all these methods, the patient is integrated into the measurement by virtue of the fact that he makes the statement as to whether and how he perceives a specific stimulus.

The electroretinogram (ERG) has become established as an objective measuring method; in this case, the reaction signal tapped from the eye with an electrode is displayed and evaluated with its time profile. Single light flashes or cyclic light/dark sequences (flicker ERG) are used for the stimulation. In this case, the mean value is determined for the total retinal area. In the recording of evoked potentials, electrodes are fitted at a specific point on the head, and the measured signal corresponds to the reaction that occurs at the measuring position via nerve cords.

Details on this have been published by J. Jörg and H. Hielscher in the book entitled "Evozierte Potentiale in Klinik und Praxis" ["Evoked Potentials in Hospitals and General Practice"]/Springer Verlag.

In order to determine the topography of the retinal sensitivity, it is fundamentally possible to stimulate partial surfaces of the retina by individual light stimuli assigned to the respective partial surface, and to measure the reaction. Since it is necessary to form mean values over a multiplicity of measurements in order to reduce the noise, this method results in an unacceptably long measurement time.

U.S. Pat. No. 5,382,987 proposes the coupling of an ophthalmoscopic system based on a 3-path Maxwell viewing system for optical examination of the retina of the eye to a perimetric system for determining the visual field, it being possible to measure the spectral sensitivity of a selected portion of the retina with the aid of the electroretinogram for which a stimulus pattern is transferred onto the retina. This method can be used to examine the sensitivity of a single portion, and to examine the overall image of the retina. An unacceptably long examination time would also result here for examining all the portions of the retina by measuring them.

The use of a laser projector provided with an optical modulator for generating a brightness pattern on the retina for measuring the pattern electroretinogram (PERG) was specified by Daniel R. Peters and John Tabora in U.S. Pat. No. 5,233,373. However, it is also possible thereby to examine only ever a selected surface of the retina, and the examination of a plurality of surfaces can be performed only sequentially.

An improved method and the associated system for determining the functional distribution of the reaction over the surface of the retina to stimuli has been specified by R. Richardson in European Patent 0 375 737. Here, the overall reaction of the retina to stimuli in the visual field is recorded, the stimuli being formed by series of patterns whose intensity varies in the horizontal direction and in the vertical direction. As an example, a sinusoidal or cosinusoidal distribution of the intensity is used, and the sensitivity distribution over the surface of the retina can be calculated by inverse transformation from the measured aggregate signals. It is disadvantageous in this method that measuring errors in the determination of the individual coefficients cannot be detected, but that individual measuring errors affect the calculation of the overall distribution function. A further disadvantage in this method is that the resolution must be adapted to the highest density of the sensitivity distribution, although this is present only in a narrowly limited region.

U.S. Pat. No. 5,539,482 specifies a method in which the stimulus pattern comprises a plurality of quadrilaterals of size increasing outward from the center and whose brightness profile is controlled with different frequencies in the range from 10 Hz to 45 Hz. In the example illustrated, 9 quadrilaterals of simultaneously modulated brightness are used, and the evaluation of the measured signal is performed with the aid of the Fourier transformation. It is true that it is possible in this case to detect the influences of the lower Ganglien cell layers by measuring the Nyquist frequency, but determining the Nyquist frequency requires carrying out a plurality of measurements with a different distribution of the modulation frequencies, and the measuring time must be selected to be so long for each frequency distribution that it is possible to determine unambiguous results for the individual frequencies. It is specified that an extension up to 32 "zones" is possible. Consequently, even in the case of this extension the method still has a very low resolution with regard to the partial surfaces that can be examined.

Another method was specified by E. E. Sutter and D. Tran in the journal Vision Research (Great Britain) Vol. 32, No. 3, pages 433 to 446, 1992, with the aid of which relatively good results were achieved. To determine the topography of the ERG components, a digital method is applied in which use is made as stimuli of hexagons whose temporal brightness profiles are controlled by m-sequences. Use is made in this case of 241 hexagons whose size increases outward from the center. Consequently, account is taken of the unequal density of the distribution function. The overall reaction signal of the eye is measured, and the signal profile is calculated for the relevant hexagon by calculating the cross-correlation function with the respective m-sequence. By weighting the signal profile with the mean value for the corresponding region of partial surfaces, interference is reduced in the determination of the amplitude, included in the signal profile, of the useful signal. To perform the measurement, use is made of m-sequences with a length of 65535 steps, which are always offset from one another by 256 steps. Given a display refresh frequency of 67 Hz, the result is an overall measuring period of approximately 16 minutes, the measurement having been subdivided into 32 time segments each being 30 seconds, plus a time for the overlap. A first disadvantage is that the method can provide exact results only to the extent that the reaction function of the retina also reacts linearly to the stimuli. However, this circumstance obtains only partially in the case of an image refresh rate of 67 Hz, and then only, again, given a short after-glow period of the display screen. A further disadvantage of this method consists in that the signal profile must be monitored subjectively, and the associated time segment must be repeated in the event of detectable interference, for example owing to blinking or given contact problems of the electrode. However, the most important disadvantage is that there is no possible way of assessing the intermediate results of the individual time segments, and that it is only at the end of the measurement, that is to say after the measured values over all time segments are present, that it is possible to determine a result and evaluate this result, and so the total measurement must be repeated when interference is not detected.

In U.S. Pat. No. 4,846,567, E. E. Sutter has already specified a basic principle of the method in which a display with a square array of elements that can be activated is used as stimuli, the temporal brightness profiles of the elements being controlled by m-sequences. The calculation of the individual reaction signals is performed with the aid of the cross-correlation function. Here, too, m-sequences of length $2^{16}-1=65535$ are applied, being offset in each case by 256 steps with reference to one another. It is likewise proposed to subdivide the overall measurement into time segments of approximately 20 to 40 seconds.

A development of this method is specified in German Patent 196 49 858, in which short and corrected m-sequences are used for controlling the light/dark sequences. Here, the individual intermediate results can be evaluated, and it is possible both to achieve a higher degree of effectiveness and an enhanced level of reliability in the evaluation of the results.

The determination of the topography of the retina of the eye from the reaction signals that result in the case of cyclic stimulation in the steady state is possible both with the method specified by E. E. Sutter and with the method specified in German Patent 196 49 858, but has the disadvantage that a poorer signal-to-noise ratio results for the same time segments, since in the case of the use of m-sequences only every second step of the measuring cycle generates a useful signal, but noise is produced in each step of the m-sequence and, in addition, it is first necessary to produce the steady state in each step of the m-sequence before an evaluation can be performed. Thus, it is therefore possible to evaluate only a portion of the reaction signals of a step, and the result in this portion is formed by two measures of noise and one measure of useful signal.

SUMMARY OF THE INVENTION

It is the object of the invention to provide a method and a system for determining the topography for reaction signals of an eye with which, in the case of cyclic stimulation in the steady state, the topography of the retina reactions can be determined in the same period with a better signal-to-noise ratio or, given a comparable signal-to-noise ratio, in a substantially shorter period.

According to the invention, the object is achieved by virtue of the fact that during the measurement the reaction signal of each partial surface can be used over the entire duration of the measurement in that each partial surface is stimulated by an integral number of oscillations, and that the number of the oscillations for the individual partial surfaces in each case differs by an integral multiple of 1. In this case, a clock pulse rate with a specific total number of clock pulses is generated in a prescribed time segment for the measurement, and from this an integral number of cycles is generated for one oscillation in each case. The generation of the oscillations for the partial surfaces is performed in the following three ways:

A mean number of oscillations is formed for a first partial surface by using the cycles generated at the clock pulse rate.

For a first group of partial surfaces a first group of oscillations is formed by prolonging the oscillations generated at the clock pulse rate at specific and largely constant intervals by individual clock pulses in each case, as a result of which a smaller number of oscillations occurs in the prescribed total number of clock pulses.

For a second group of partial surfaces a second group of oscillations is formed by shortening the oscillations generated at the clock pulse rate at specific and largely constant intervals by individual clock pulses in each case, as a result of which a larger number of oscillations occurs in the prescribed total number of clock pulses.

Within each group, use is made for the partial surfaces of a different interval for the prolongation or shortening by one clock pulse, and the number of these clock pulses is in each case an integral multiple of the number of the clock pulses used for the mean oscillation. A plurality of additional oscillations before the time interval for the measurement are provided for reaching the steady state, and at least one additional oscillation after the time interval for the measurement is provided for evaluating the last oscillation. The aggregate signal that is formed from the superimposition of the reaction signals of all the partial surfaces is tapped at the patient and is fed, amplified and filtered, to an analog-to-digital converter that accepts the signal with the same clock pulses used for generating the oscillations. The recovery of the reaction signals for the individual partial surfaces is performed by cyclic summation of the successive portions of the aggregate signal, use being made for the summation of the same cycles as for the oscillations for stimulating the corresponding partial surfaces.

The system for carrying out the method according to the invention is achieved by means of the features named in claim 8. Advantageous refinements are specified in the subclaims.

The advantage of the solution according to the invention consists in that it is an objective measuring method, that is to say the measurement is performed independently of whether and how the person perceives which stimulus. A further advantage of the solution according to the invention is the high resolution with regard to the partial surfaces, to be examined, of the retina, which are examined simultaneously, as a result of which there is a short measuring time and it is possible to evaluate intermediate results, a high reliability thereby being achieved for the intermediate results. Moreover, the solution according to the invention has the advantage that during measurement in the steady state (steady-state signals) the steady state is maintained over the entire measuring time and, in particular, that a useful signal is generated from all partial steps of the measuring cycle, the result being a substantially better signal-to-noise ratio.

The solution according to the invention is to be explained in more detail with the aid of an exemplary embodiment. In the associated drawing:

BRIEF DESCRIPTION OF THE DRAWINGS

FIG. 5 shows a table with practical values of the oscillations, and

DESCRIPTION OF THE PREFERRED EMBODIMENTS

Figure 1:
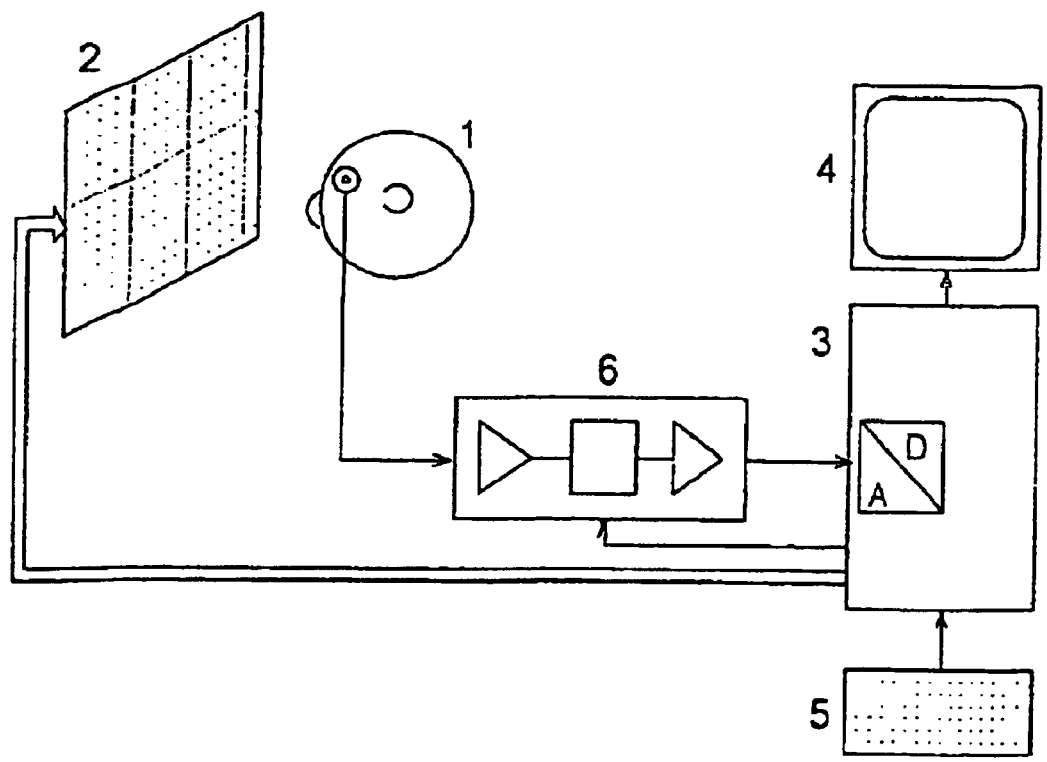
FIG. 1 shows the design principle of the solution according to the invention.

The principle of the design of the system used for the measurement is illustrated in FIG. 1. A patient 1 looks at a stimulator 2 that generates a luminous image that is projected onto the retina of the eye. The light/dark control of the partial surfaces of the stimulator 2 is performed via a control unit 3. The operation of the system, that is to say setting the measurement parameters and the evaluation methods, is performed via a keyboard 5 connected to the control unit 3. The operator prompting and the evaluation of the results are performed via a display unit 4 connected to the control unit 3. The reaction signal tapped at the patient 1 is fed via an amplifier 6 to the analog-to-digital converter 7 arranged in the control unit 3. The amplifier 6 includes a plurality of amplifier stages and a bandpass filter and its parameters can be programmed via the control unit 3.

Oscillations are used to control the individual partial surfaces of the stimulator 2 through light and dark cyclically, a different number of oscillations being used for each partial surface in a prescribed period.

The principle is explained by a simple numerical example:
starting from a 30 Hz flicker stimulation, $N_1=300$ oscillations then result for a period of 10 seconds. This stimulation is used for the first partial surface. In the same period, a second partial surface receives $N_2=299$ oscillations, and a third partial surface receives $N_3=301$ oscillations. The following frequencies result with these values: $f_1=30$ Hz, $f_2=29.9$ Hz and $f_3=30.1$ Hz. Each partial surface i of the retina generates a reaction signal r that comprises the fundamental wave of the stimulation and corresponding harmonic waves:

$$r_1=r_{11}\cdot\sin(2\pi\cdot 30\ Hz\cdot t)+r_{12}\cdot\sin(2\pi\cdot 60\ Hz\cdot t)+\ldots$$

$$r_2=r_{21}\cdot\sin(2\pi\cdot 29.9\ Hz\cdot t)+r_{22}\cdot\sin(2\pi 59.8\ Hz\cdot t)+\ldots$$

$$r_3=r_{31}\cdot\sin(2\pi\cdot 30.1\ Hz\cdot t)+r_{32}\cdot\sin(2\pi\cdot 60.2\ Hz\cdot t)+\ldots$$

The measured signal corresponds to the sum of the individual components. If the reaction signal measured over 10 seconds is now divided into 300 portions and the cyclic sum of these portions is formed, the result is the reaction signal of the first partial surface:

$$R_1=300\cdot r_1=300\cdot(r_{11}\cdot\sin(2\pi\cdot 30\ Hz\cdot t)+r_{21}\cdot\sin(2\pi\cdot 60\ Hz\cdot t)+\ldots)$$

The other components generate no signal during the cyclic addition, since their fundamental wave and all harmonic waves are always added with a different phase angle over one or more full oscillations.

The reaction signal of the second partial surface is obtained similarly in the case of a division of the signal measured over 10 seconds into 299 portions, and the reaction signal of the third partial surface is obtained similarly in the case of a division into 301 portions. The respective other signal components do not influence the results. The difference consists only in the fact that the individual reaction is calculated once 300-fold, once 299-fold and once 301-fold.

However, this deviation may be corrected by a simple conversion using the corresponding coefficients.

The deviations from the nominal frequency 30 Hz are +/−0.33% and therefore exert virtually no influence on the result.

However, the method can be applied only when fully complete oscillations are used in the time segment considered. This condition is met whenever all the oscillations used are derived from a basic raster.

Figure 2:
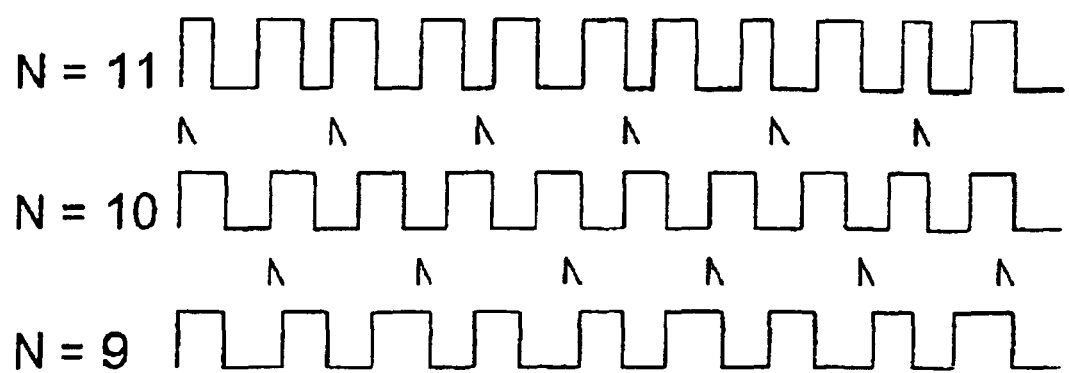
FIG. 2 shows a timing diagram for the generation of the oscillations.

FIG. 2 shows a timing diagram for the generation of the oscillations. In this example, square-wave oscillations are derived from a basic raster with 60 clock pulses. The curve illustrated in the middle has the nominal oscillating frequency of N=10, that is to say each oscillation includes 6 clock pulses. Shortening by single clock pulses at the six marked points produces the curve with 11 oscillations that is shown at the top. If the oscillations are prolonged by one clock pulse in each case at the six marked points, this being done by prolonging the state present at this instant by one clock pulse, the result is N=9 oscillations in the same period. If always complete oscillations are considered, the signal profile can also be described by specifying the length of oscillation if the course from higher level to lower level is always designated as one oscillation.

N=11 comprises 6 oscillations relating to 5 clock pulses (3 times 2+3 clock pulses, 3 times 3+2 clock pulses) and 5 oscillations relating to 6 clock pulses.

N=10 comprises 10 oscillations relating to 6 clock pulses.

N=9 comprises 6 oscillations relating to 7 clock pulses (3 times 4+3 clock pulses, 3 times 3+4 clock pulses) and 3 oscillations relating to 6 clock pulses.

Of course, the differences between the in each case two lengths of oscillation can clearly be recognized in the case of so coarse a clock pulse raster. If more clock pulses are used per oscillation together with a larger number of oscillations, the differences also become smaller, and all the oscillations can be considered as virtually continuous.

Figure 3:
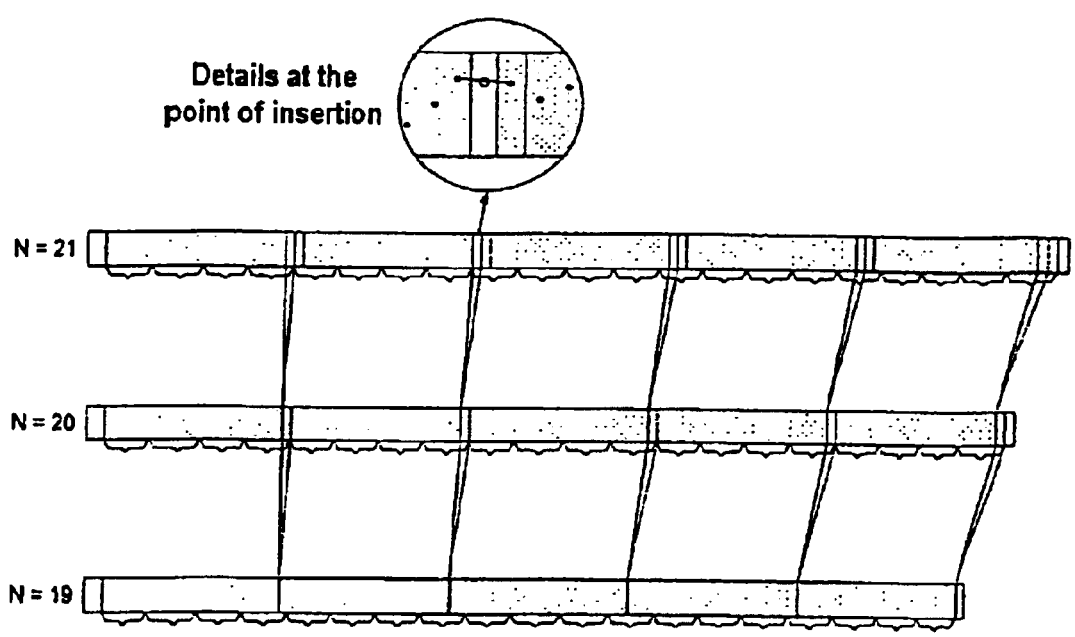
FIG. 3 shows a diagram relating to the principle of the cyclic addition.

The principle of cyclic addition is illustrated in FIG. 3.

Here, an example is selected with N=20 oscillations relating in each case to 5 clock pulses. N=20 symbolizes the signal profile, which was read in as aggregate signal via the path of electrode-amplifier-analog-to-digital converter. It is illustrated symbolically here the a settling region is present upstream of the actual signal portion hatched in, and at least one oscillation is appended at the end, in order still to be able to evaluate the large reaction signal without errors. The cycle lengths with n=5 clock pulses for the cyclic summation is specified below the hatched portion. Only the signal that was stimulated with N=20 is obtained with this summation.

Shown symbolically at the top in FIG. 3 with the designation N=21 is the signal profile that is produced by inserting clock pulses at the points that were shortened by one clock pulse during the generation of the oscillations. It is illustrated here in an enlarged fashion how the signal level for the inserted clock pulse is formed as mean value from the preceding and the subsequent signal level. The insertion of the clock pulses results in the longer signal string with N=21 oscillations relating to in each case 5 clock pulses. If the cyclic summation is also carried out here with N=21 cycles relating to n=5 clock pulses, only the signal that was stimulated with N=21 is obtained.

Shown symbolically at the bottom in FIG. 3 with the designation N=19 is the signal profile that is produced by removing clock pulses at the points at which the oscillations were prolonged by one clock pulse during the generation. The removal of the clock pulses produces the shorter signal string with N=19 oscillations relating to in each case 5 clock pulses. If the cyclic summation is also carried out here with N=19 cycles relating to n=5 clock pulses, only the signal that was stimulated with N=19 is obtained.

Figure 4:
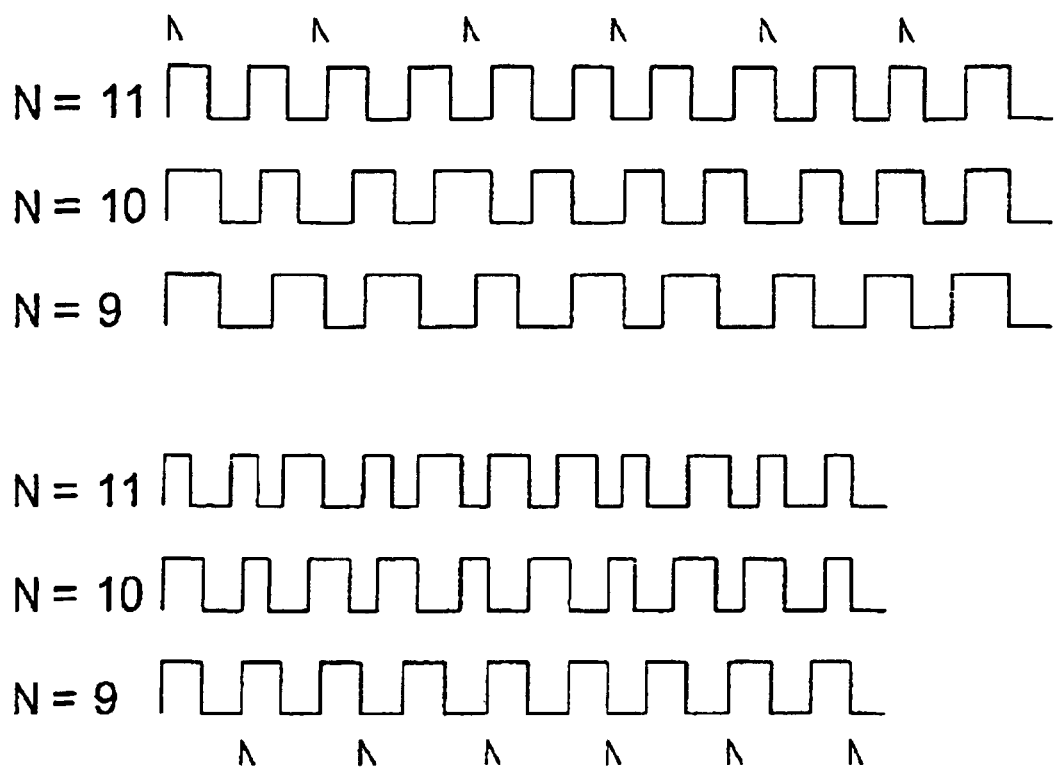
FIG. 4 shows a timing diagram for the cyclic addition.

FIG. 4 shows a timing diagram for the cyclic addition, the same stimulation signals having been used as in FIG. 2, that is to say a signal with N=10 oscillations and n=6 clock pulses from which signals with N=11 and N=9 oscillations were also derived. The conversion of the signals is performed using the same principle as illustrated in FIG. 3. In order to recover the signal N=11, in the upper part of FIG. 4 clock pulses are inserted at the points at which shortening of the oscillation by one clock pulse was carried out during the generation and, in order to recover the signal N=9, in the lower part of FIG. 4 clock pulses are removed where the oscillation was prolonged by one clock pulse during the generation. The points at which the prolongations of the clock pulse rate were undertaken are drawn in. If the reaction signal is equated to the stimulation signal, the illustrated signal profiles then represent the components of the reaction signal. The curve with N=11 results in the upper part, and the curve with N=9 in the lower part, again with an oscillation of initial length n=6. That is then also the basis for the cyclic addition.

It should be pointed out at this juncture that as early as in FIG. 2 the positions for the shortening of the oscillation by one clock pulse are drawn in in a fashion offset by one oscillation with reference to the position for the prolongation of the oscillation by one clock pulse. Such an offset, or a similar one, is necessary in order to ensure that when converting for the cyclic addition the partial segments that have already been prolonged or shortened once during generation of the oscillations are not prolonged or shortened again by one clock pulse.

A practical application of the above-named principle requires working with a larger number of clock pulses per oscillation and with a larger number of oscillations in the period prescribed for the measurement. Considering once again a stimulation with a 30 Hz flicker signal, the following values are sensible:
clock frequency 2 kHz.

The sampling frequency is 0.5 ms in order to obtain a rigid coupling of stimulation and recording of the reaction signal, that is to say clocking of the analog-to-digital converter.

An oscillation can be formed from 66 or 67 clock pulses. It is advantageous to use 67 clock pulses, since 67 itself is a prime number and this thus ensures that the number of the oscillations has no common divisor with 67, and thus the prolongation or shortening by one clock pulse is distributed uniformly over all the clock pulses of the oscillation in the overall cycle. Consequently, the error owing to the removal or insertion of clock pulses occurs equally often at all the points of the oscillation, and the error is eliminated virtually completely. The change by one clock pulse is a deviation by 1.5% from the nominal value in the case of 67 clock pulses, from which it follows that a change by two clock pulses corresponds to a deviation of 3% from the nominal value. If the aim is to generate a symmetrical oscillation in the case of 67 clock pulses, it is then necessary to operate half the oscillations with a pulse duty factor high:low=33:34, and the other half with a pulse duty factor high:low=34:33.

If a measuring period of 35 seconds is used, then 1050 oscillations result in the case of 30 Hz. Consequently, it is possible to generate 61 different oscillations in the case of a deviation of 3% from the nominal value, that is to say it is possible to control 61 different partial surfaces.

FIG. 5 shows a table with practical values of the oscillations under the said conditions. It can be seen that for N=1050 only oscillations with 67 clock pulses occur. For N=1051, there are 67 oscillations with 66 clock pulses, that is to say the oscillation was shortened 67 times by one clock pulse in each case, and there are 984 oscillations with 67 clock pulses. Thus, all the oscillations are derived from 70350 clock pulses. The spacing of the clock pulses to be faded out or faded in is specified in the last column. This spacing is yielded for an oscillating frequency $N_1$ from:

$$\text{Spacing} = \frac{1050}{|N_i - 1050|}.$$

For the cases in which no integral value results for the spacing, the points are yielded from the rounded value of the multiple spacing. Consequently, all the oscillating frequencies between 1020 and 1080 can be derived. Only the integral values of this spacing are entered in the table.

Given a larger number of oscillations, it is also possible to generate still more different oscillations in conjunction with the same permissible deviation from the nominal value of the oscillation. Assuming that the 3% limit is not exceeded, it is then possible to derive 103 different oscillations with 1750 oscillations, that is to say a measuring period of approximately 58.45 seconds, that is to say 103 partial surfaces can be controlled.

It is a condition for applying this method that the state of the stimulator, that is to say of the image illustrated, can vary in a spacing of 0.5 msec. All parts of the image must be switched over synchronously in the process. This is possible only with a surface fitted with LEDs. A range of variants can be used here:

The LEDs are arranged and interconnected in the way in which the partial surfaces are to be illustrated. This is certainly simpler but, in return, not flexible.

Each LED element is driven separately, and partial surfaces are formed by the interaction of neighboring elements. This is certainly more complicated, but, in return, flexible.

Figure 6:
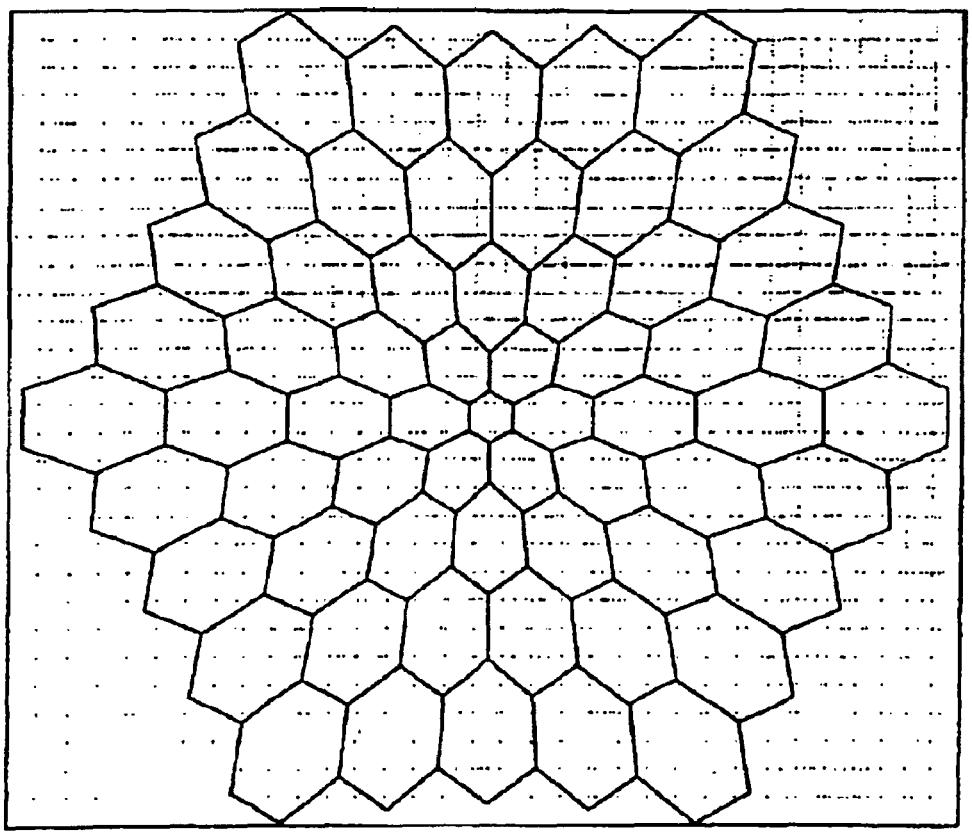
FIG. 6 shows an LED surface with an image of 61 hexagons.

FIG. 6 shows how it is possible to represent an image with 61 hexagons on a surface fitted with 33×29=957 LEDs. The assignments of the LEDs to the partial surfaces can be calculated by evaluating the associated surface fractions of the LEDs relative to the partial surfaces of the image.

Stimulators with a serial representation of the image as in the case of a display screen, a laser scanner or an LCD display screen are not suitable for this method.

Using this method, the following cycle is yielded for an example in which the stimulating image comprises 61 hexagons and the stimulation is performed with a 30 Hz flicker signal.

Generated in the control unit 3 that is illustrated in FIG. 1 is a clock pulse rate at 2 kHz, from which the 30 Hz signal with 67 clock pulses per oscillation is formed. This clock pulse rate comprises three sequential portions:

A first portion from which an oscillation is derived that serves the purpose of producing the steady state and adapting the eye. This portion includes, for example, 15 oscillations at 30 Hz.

A second portion that is used for the measurement. This portion includes 1050 oscillations in the case of the mean frequency of 30 Hz and comprises 67×1050= 70350 clock pulses.

A third portion in which at least one more oscillation is generated and which serves the purpose of still detecting the last oscillation of the measurement without errors.

67 clock pulses are now used for each mean oscillation in order to count the 30 Hz oscillation. Of these, for a pulse duty factor of 1:1 half of the oscillations are generated with 34 high clock pulses and 33 low clock pulses, and the other half of the oscillations are generated with 33 high clock pulses and 34 low clock pulses. The oscillations thus generated serve in the first and in the third portion of the clock pulse rate as stimulation signal for all partial surfaces. In the second portion, the oscillation thus generated is used only for one partial surface. For a second partial surface, one clock pulse less is used in each case in the spacing of 1050:1=1050 clock pulses. That is to say, the first oscillation is shortened by the first clock pulse and comprises only 66 clock pulses. The next shortening of an oscillation is performed at clock pulse number 1051, then at clock pulse number 2101 and so on. This produces in the clock pulse rate of 70350 clock pulses 1051 oscillations that include small jumps with an error of 1.5% at the spacing of 1050 clock pulses. However, these jumps occur 67 times over the overall sequence and always in this case at a different point of the oscillation, since 67 is a prime number. Here, the total error is the 1050th part of 1.5% and is therefore negligible. The principle is shown in FIG. 2 for a greatly simplified example with 11 oscillations that consist in each case of 6 clock pulses.

One clock pulse less is used for a second partial surface at the spacing of 1050:2=525 clock pulses. This results in 1052 oscillations in the clock pulse rate. The spacing is 1050:3=350 clock pulses for a third partial surface, and 1050:4=262.5 clock pulses for a fourth partial surface. If this value is calculated with rounding, the spacing is alternately 263 and 262 clock pulses. Different oscillating frequencies of 1051 to 1080 are generated in this way in the clock pulse rate. It holds in general for the position A of the clock pulse to be inserted that:

$$A = A_0 + n(1050 : \Delta N)$$

Here, $A_D$ is the position of the first clock pulse to be inserted, $\Delta N$ is the deviation of the oscillating frequency from 1050, and n is the serial number for the clock pulse to be inserted, the expression in brackets always being rounded. The associated numerical values are represented in FIG. 5 as a table, only the integral values for the spacing being entered. The frequency at 1050 oscillations is 30 Hz and rises up to 30.857 Hz at 1080 oscillations.

1049 oscillations can be generated using the same principle by prolonging an oscillation by in each case one clock pulse at the spacing of 1050:1=1050 clock pulses in the clock pulse rate of 70350 clock pulses. In this case, the first prolongation is carried out at clock pulse number 35, the second at clock pulse number 1085, etc. This principle is illustrated in FIG. 2 for N=9. 1048 oscillations result when use is made of a spacing of 1050:2=525 clock pulses. 1020 oscillations in the clock pulse rate of 70350 clock pulses are obtained for a spacing of 1050:30=35 clock pulses. The associated numerical values are specified in FIG. 5.

61 different rates that have a constant clock pulse length of 70350 clock pulses result from this calculation. Each of these rates comprises an integral number of oscillations. The stimulator 2 illustrated in FIG. 1 is controlled with the frequency of 2 kHz. The stimulator 2 comprises an array of light-emitting diodes which is used to generate the image used for the stimulation. FIG. 6 shows an example in which hexagons are drawn in as partial surfaces, and the assignment to the partial surfaces is performed such that each light-emitting diode is assigned to that hexagon in which the majority of its area is included. All the light-emitting diodes of a partial surface are controlled in this case with the same signal string, and all the diodes of the overall image are controlled with the same clock pulse.

If the patient now looks at this image generated by the stimulator, corresponding reaction signals are generated by the individual partial surfaces of the retina. The sum of these reaction signals are amplified as aggregate signal, tapped at the cornea of the eye with the aid of an electrode, filtered and fed to an analog-to-digital converter. This analog-to-digital converter is controlled with the same clock pulse with which the light-emitting diodes are also controlled. Consequently, the tapped signal is brought into the same clock grid as was used for generating the stimulation image.

The reaction signals of the individual partial surfaces can now be recovered from this aggregate signal. The aggregate signal is added cyclically, specifically with a cycle of 67 clock pulses, for the reaction signal whose partial surface was stimulated with 1050 oscillations. This results in the 1050-fold multiple of the reaction signal of this partial surface. All other reaction signals are displaced in the case of this addition by one or more oscillations, and therefore make no contribution to the result, since a signal free from direct voltage always has components of equal size in the positive and negative range.

The distortion undertaken in the generation of the stimulation signal is canceled again for the purpose of recovering the reaction signals of the other partial surfaces. That is to say, in order to recover the signal of the partial surface stimulated with 1051 oscillations, one clock pulse whose value comprises the mean value of the preceding and the subsequent sample is now inserted at those points at which a shortening by one clock pulse was undertaken. The signal string is thereby prolonged to 70350+67 clock pulses and thus to 1051 oscillations of 67 clock pulses in each case. Applying the cyclic addition thereupon then produces the 1051-fold multiple of the reaction signal considered. All other components make no contribution to the result. The principle is illustrated in FIG. 3 in the upper part for N=21. The fact that signals are produced in this case that correspond to the mean stimulation rate of 1050 oscillations is shown in a simplified way in FIG. 2 in the upper part, in which the clock pulses were inserted for N=11. A similar procedure of inserting clock pulses is adopted for recovering the reaction signals of the other partial surfaces with an oscillating frequency >1050.

The recovery of the signal with 1049 oscillations is performed such that one clock pulse is now removed at those points at which the stimulation signal was prolonged. The result is a signal string that comprises 70350−67 clock pulses, and thus 1049 oscillations relating to 67 clock pulses. The 1049-fold multiple of the reaction signal of the relevant partial surface results from the cyclic addition. The principle is illustrated in FIG. 3 for N=19. The fact that signals are again produced in this case that correspond to the mean stimulation rate of 1050 oscillations is shown in a simplified fashion in FIG. 2 in the lower part, in which the clock pulses have been removed for N=9.

The jumps produced in this case are always produced over the entire rate at a different point in the 67 clock pulses and therefore produce virtually no error.

The evaluation of the measurement results can be performed by determining the amplitude and the latency of the peak value. Furthermore, the signal components of the fundamental wave and the harmonic wave and their phase angle can be determined with the aid of the Fourier transformation. It is possible in this case to make use of the advantage that a stimulation signal is being employed in which specific signal components are not, or virtually not, included, such as, for example, in the case of a square-wave signal with the pulse duty factor 1:1, in which the first harmonic wave is not included. This results in favorable conditions for drawing conclusions on nonlinearities in the reaction signal.

The method can also be applied advantageously to all other measurements in which use is made of cyclic stimulation and a steady state. The number M of the partial results that can be measured in parallel over the entire measuring period T in conjunction with a permissible tolerance Δ of the stimulation frequency f is:

$$M \leq 1 + 2 \cdot \Delta \cdot f \cdot T$$

LIST OF REFERENCE NUMERALS

1 Patient
2 Stimulator
3 Control unit
4 Display unit
5 Keyboard
6 Amplifier
7 Analog-to-digital converter

We claim:

1. A method for determining the topography for the reaction signals of an eye, by simultaneously measuring the reaction signals that are generated by a plurality of partial surfaces of the retina of an eye by light stimuli and that are produced in the steady state in the case of cyclic excitation, wherein each partial surface is stimulated by an integral number of complete oscillations of the light stimuli in a prescribed time interval for the measurement, and wherein the number of the oscillations in the prescribed time interval for the individual partial surfaces in each case differs by an integral multiple of 1 by virtue of the fact that there is formed in a prescribed time interval for the measurement a clock pulse rate with a specific total number of clock pulses from which an integral number of cycles with one oscillation in each case is counted, and wherein the generation of the oscillations for the partial surfaces is performed in such a way that a mean number of oscillations is formed for a first partial surface by using the cycles generated at the clock pulse rate, for a first group of partial surfaces a first group of oscillations is formed by prolonging the generated cycles at specific and largely constant intervals by individual clock pulses, as a result of which a smaller number of oscillations occurs in the prescribed total number of clock pulses, that for each of the partial surfaces assigned to this group a different interval is used for the prolongation by a clock pulse, and that the number of the clock pulses used for the prolongation is in each case an integral multiple of the number of the clock pulses used for the mean number of oscillations, and for a second group of partial surfaces a second group of oscillations is formed by shortening the generated cycles at specific constant intervals by individual clock pulses, as a result of which a larger number of oscillations occurs in the prescribed total number of clock pulses, that for each of the partial surfaces assigned to this group a different interval is used for the shortening by a clock pulse, and the number of the clock pulses used for the shortening is in each case an integral multiple of the number of the clock pulses used for the mean oscillation, and wherein a plurality of additional oscillations before the time interval for the measurement are provided for reaching the steady state, and at least one additional oscillation after the time interval for the measurement is provided for evaluating the last oscillation, wherein an aggregate signal that is formed from the superimposition of the reaction signals of all the partial surfaces is tapped at the patient and is fed, amplified and filtered, to an analog-to-digital converter that accepts the signal with the same clock pulses used for generating the oscillations, and wherein the reaction signals for the individual partial surfaces are recovered by cyclic summation of the successive portions of the aggregate signal, use being made for the summation of the same cycles as for the oscillations for stimulating the corresponding partial surfaces.

2. The method as claimed in claim 1, wherein for the cyclic addition for recovering the reaction signals for the individual partial surfaces use is made of the cycles that were used to generate the mean number of oscillations for the light stimuli, and wherein, during the cyclic addition, for the oscillations that were prolonged by one clock pulse in each case a sample is removed at the point at which the oscillation was prolonged by an additional clock pulse during the generation, and for the cycles during which the oscillation was shortened by one clock pulse an additional value is inserted at this point that corresponds to the mean value from the preceding and the subsequent sample.

3. The method as claimed in claim 1, wherein the cycles for generating the light stimuli include sinusoidal oscillations.

4. The method as claimed in claim 1, wherein the cycles for generating the light stimuli include square-wave oscillations whose pulse duty factor can be set.

5. The method as claimed in claim 1, wherein the Fourier transformation is applied for recovering the fundamental and harmonic waves of the reaction signals for the individual partial surfaces.

6. The method as claimed in claim 1, wherein the reaction signal is an electroretinogram that is taken with an electrode on the cornea of the eye.

7. The method as claimed in claim 1, wherein the reaction signal is a visually evoked potential that is taken with one or more electrodes on the patient's head.

8. A system for determining the topography for the reaction signals of an eye, by simultaneously measuring the reaction signals that are generated by a plurality of partial surfaces of the retina of an eye by light stimuli and that are produced in the steady state in the case of cyclic excitation, comprising means for generating light stimuli on partial surfaces of the retina of the eye, which can be controlled by signals, a control unit having means for generating the signals for controlling the light stimuli that generate an integral number of oscillations in a prescribed time interval for all partial surfaces, the number of the oscillations for each partial surface differing in the prescribed time interval by an integral multiple of 1, and the oscillations being forced from a prescribed total number of clock pulses, and having means for fading in clock pulses at constant or virtually constant intervals for A first group of oscillations, and for fading out clock pulses for a second group of oscillations, and having means for counting the clock pulses to be faded in and faded out, having an analog-to-digital converter for accepting the aggregate signal that is clocked with the clock pulse for generating the control signals, and having means for the cyclic addition of the digitized aggregate signal, there being removed in each case a measured value at the point at which there was prolongation by one clock pulse upon the signal for controlling the light stimuli, and there being inserted in each case a measured value at the point at which there was shortening by one clock pulse upon the signal for controlling the light stimuli, and means for storing the measurement results, means for tapping an aggregate signal, generated by the cyclic stimulation, at the patient to be examined, amplifying and filtering said signal and feeding it to the analog-to-digital converter in the control unit, and means for handling, monitoring and evaluating the measurement results.

9. The system as clamed in claim 8, wherein the light stimuli are generated on the retina by an array of light-emitting diodes whose brightness profile can be controlled individually or in groups by signals.

10. The system as claimed in claim 6, wherein the control unit includes a computer, that calculates the oscillations for controlling the brightness profile of the partial surfaces.

generates the control signals for controlling the LED array for generating the light stimuli, controls the analog-to-digital converter, stores the digitized aggregate signal, calculates and stores the reaction signals of the partial surfaces by cyclic summation, and displays and evaluates the results and via which the operation of the system and setting of the parameters of the amplifier are performed.

* * * * *